US 12,419,595 B2

United States Patent
Lemoine

(10) Patent No.: US 12,419,595 B2
(45) Date of Patent: Sep. 23, 2025

(54) BACKSCATTERED X-PHOTON IMAGING DEVICE

(71) Applicant: THALES, Courbevoie (FR)

(72) Inventor: Thierry Lemoine, Velizy-Villacoublay (FR)

(73) Assignee: THALES, Courbevoie (FR)

( * ) Notice: Subject to any disclaimer, the term of this patent is extended or adjusted under 35 U.S.C. 154(b) by 120 days.

(21) Appl. No.: 18/018,524

(22) PCT Filed: Apr. 19, 2021

(86) PCT No.: PCT/EP2021/060136
§ 371 (c)(1),
(2) Date: Jan. 27, 2023

(87) PCT Pub. No.: WO2022/022868
PCT Pub. Date: Feb. 3, 2022

(65) Prior Publication Data
US 2023/0293126 A1     Sep. 21, 2023

(30) Foreign Application Priority Data

Jul. 30, 2020   (FR) ........................... 2008069

(51) Int. Cl.
*A61B 6/42*    (2024.01)
*A61B 6/06*    (2006.01)
*A61B 6/40*    (2024.01)

(52) U.S. Cl.
CPC ............. *A61B 6/4241* (2013.01); *A61B 6/06* (2013.01); *A61B 6/4007* (2013.01)

(58) Field of Classification Search
CPC ....... A61B 6/06; A61B 6/4241; A61B 6/4007; A61B 6/4291; A61B 6/483; A61B 6/032; A61B 6/4035; A61B 6/4266; A61B 6/405; A61B 6/4208; A61B 6/5205; A61B 6/5282; A61B 6/502; A61B 6/481; A61B 6/482; A61B 6/5217; A61B 6/585; A61B 6/4078;
(Continued)

(56) References Cited

U.S. PATENT DOCUMENTS 4,875,227 A    10/1989   Rossi et al.
6,553,096 B1 †   4/2003   Zhou
(Continued)

FOREIGN PATENT DOCUMENTS

CN    1756508 A    4/2006
JP    H5-56962 A    3/1993
(Continued)

OTHER PUBLICATIONS

English translation of the Chinese Office Action issued in Chinese patent application No. 202180053378.6 dated May 22, 2025.
(Continued)

*Primary Examiner* — Irakli Kiknadze
(74) *Attorney, Agent, or Firm* — BakerHostetler

(57) ABSTRACT

An imaging device employing backscattered x-ray photons, includes a plurality of x-ray sources, all configured to irradiate an analysis region wherein an object to be imaged may be placed, and a pixelated x-ray detector placed so as to detect x-ray photons potentially scattered by the object.

9 Claims, 3 Drawing Sheets

(58) Field of Classification Search
CPC .............. A61B 6/4233; G01N 23/203; G01N 23/20008; G01N 23/20025; G01N 2223/1016; G01N 2223/40; G01N 2223/053; G01N 2223/301; G01N 23/04; G01N 23/20083; G01N 2223/045; G01N 23/046; G01N 23/20; G01N 2223/616; G01N 23/005; G01N 23/201; G01V 5/0025; G01V 5/222; G01V 5/224; G01V 5/223; G01V 5/0016; G01V 5/12; G01V 5/0033; G01V 5/0041; G21K 1/025; G21K 1/043; H05G 1/06; H05G 1/02; G01T 1/2985; G01T 1/36; G01T 1/1645; G01T 1/29; G01T 1/2921; G01T 1/242; G06T 11/006; G06T 2211/408; G06T 15/04; G16H 50/30
USPC ......................... 378/70, 76, 86–90, 147–160
See application file for complete search history.

(56) References Cited

U.S. PATENT DOCUMENTS

| | | | |
|---|---|---|---|
| 6,876,724 B2 † | 4/2005 | Zhou | |
| 7,231,017 B2 † | 6/2007 | Gertsenshteyn | |
| 2004/0218714 A1 † | 11/2004 | Faust | |
| 2006/0182217 A1 | 8/2006 | Harding et al. | |
| 2007/0258562 A1* | 11/2007 | Dinca | G01N 23/203 378/62 |
| 2013/0039472 A1* | 2/2013 | Morton | G01V 5/223 378/88 |
| 2016/0003965 A1* | 1/2016 | Chen | G01V 5/222 378/87 |
| 2017/0052125 A1* | 2/2017 | Georgeson | G01N 23/20025 |
| 2017/0219501 A1* | 8/2017 | Yakimov | A61B 6/4208 |
| 2017/0336526 A1* | 11/2017 | Arodzero | G01V 5/232 |
| 2019/0099139 A1 | 4/2019 | Yamazaki | |
| 2021/0030383 A1* | 2/2021 | Samant | A61B 6/466 |
| 2021/0086441 A1* | 3/2021 | Georgeson | B29C 64/393 |
| 2021/0208086 A1* | 7/2021 | Safai | G01N 23/203 |
| 2021/0372949 A1* | 12/2021 | Schubert | G01V 5/22 |

FOREIGN PATENT DOCUMENTS

| | | |
|---|---|---|
| JP | 2011-229605 A | 11/2011 |
| WO | 2004/078043 A1 | 9/2004 |
| WO | 2008/063695 A2 | 5/2008 |
| WO | 2015/106893 A1 | 7/2015 |
| WO | 2019/011980 A1 | 1/2019 |

OTHER PUBLICATIONS

European Search Report issued in European Patent Application No. 21 719 636.9 dated Jun. 12, 2025.
Choi et al "Coded aperture computed tomography." Adaptive Coded Aperture Imaging, Non-Imaging, and Unconventional Imaging Sensor Systems. vol. 7468. SPIE, 2009.†

\* cited by examiner
† cited by third party

BACKSCATTERED X-PHOTON IMAGING DEVICE

CROSS-REFERENCE TO RELATED APPLICATIONS

This application is a National Stage of International patent application PCT/EP2021/060136, filed on Apr. 19, 2021, which claims priority to foreign French patent application No. FR 2008069, filed on Jul. 30, 2020, the disclosures of which are incorporated by reference in their entirety.

FIELD OF THE INVENTION

The invention relates to an imaging system employing x-ray photons. Most x-ray imaging systems operate in transmission, as is the case with conventional radiography. More precisely, some of the incident x-ray photons irradiating an object to be imaged are absorbed by the object. The image is obtained using unabsorbed the x-ray photons having passed through the object, which is placed between the x-ray source and the detector. In certain situations, this type of radiology does not allow an image to be obtained. This is in particular the case in the context of inspection of a piece of luggage abandoned against a wall. It is then impossible to place the object between the source and the detector. This is also the case in the presence of a substance that is opaque to x-rays, which appears as a uniform region in conventional radiography. Imaging using backscattered photons allows these situations to be addressed. This type of imaging takes advantage of the interaction between incident x-ray photons and the material from which the objects to be imaged are formed. A number of effects cause photons to scatter in all directions and in particular in the direction of the source of incident radiation. Among the identified physical effects, Rayleigh and Compton scattering are principally of note.

BACKGROUND

Nevertheless, the uptake of imaging using backscattered photons has nevertheless been slow because image formation is difficult. The main reason is that, for photons the energy of which is comprised between 1 and 1000 keV, it is not possible to produce devices that operate in a similar way to optical focusing devices. The refractive index is too low to produce lenses, and the transparency of metals at these energies prevents the production of mirrors.

However, a plurality of techniques for producing an image from backscattered photons have been developed. A first technique consists in irradiating the object to be imaged by means of a fine beam of x-ray photons and in moving the beam to cover the entire object. This technique is known as the flying-spot technique. At any given time, only a narrow region of the object is capable of emitting backscattered photons. It is then enough to collect all the emitted photons, irrespectively of their origin, using a detector with a single pixel. The image is reconstructed by scanning the entirety of object by moving the beam of x-ray photons. The resolution of the obtained image is given by the geometry of the beam.

A second technique consists in irradiating the object in its entirety with x-ray photons and in using a pixelated and collimated detector to collect the backscattered photons. The collimator placed in front of each pixel of the detector is sufficiently anisotropic for each pixel to receive only photons from a region of the object located facing. The resolution of the image is then given by the detector and its collimator.

A third technique also consists in irradiating the object in its entirety and in using a pixelated detector. Unlike the second technique, this third technique does not use a collimator but rather an absorbing plate pierced with a hole, and hence this technique is called the pin-hole technique.

The pin-hole technique has the advantage of simplicity. The size of the hole is the most important parameter as regards the quality of the obtained image. To a first approximation, the hole diameter must be of the same order of magnitude, or even smaller, than the size of the pixels of the detector. A larger hole would result in a degradation of the resolution of the image. In contrast, the flux of photons passing through a hole remains of low intensity, this leading to a signal-to-noise ratio that may be too low to obtain a usable image. In other words, to improve the signal-to-noise ratio, the dimensions of the hole must be increased, this degrading the spatial resolution of the image. The quality of the image is the result of a compromise between resolution and signal-to-noise ratio.

To increase the signal-to-noise ratio, one solution consists in increasing the amount of incident photons emitted by the source, this allowing the number of backscattered photons to be increased proportionally. However, certain objects are subject to maximum doses of radiation, particularly in medical imaging. In addition, x-ray sources are also limited in the doses they are able to emit. These sources are essentially limited by thermal factors. The more radiation the source emits, the more it is heated. In the case of autonomously powered portable imaging systems, the emission of radiation is also limited by the batteries of the system.

Another limitation of the pin-hole technique lies in the geometry of the imaging system. In the object to be imaged, the regions closest to the source receive more incident radiation than the regions furthest away. The amount of backscattered radiation is therefore a function of the distance to the source. In addition, the amount of backscattered radiation is also a function of an angle made between a direction passing through the source and the point of the object struck by the incident radiation and a direction passing through this point and the hole in the absorbing plate. These two geometric characteristics lead to an intrinsic non-uniformity in the distribution of backscattered photons over the surface of the detector, independently of the object to be imaged.

SUMMARY OF THE INVENTION

The invention aims to overcome all or some of the aforementioned problems by providing an imaging device employing backscattered x-ray photons that allows the quality of the obtained images to be improved by irradiating an object to be imaged by means of a plurality of distinct x-ray sources.

Irradiation of the object with a plurality of distinct sources allows the uniformity of the flux of incident photons reaching the object to be improved both in respect of intensity and in respect of angle of irradiation.

To this end, the subject of the invention is an imaging device employing backscattered x-ray photons, comprising:
 a plurality of x-ray sources, all configured to irradiate an analysis region in which an object to be imaged may be placed, a pixelated x-ray detector configured to simultaneously collect a plurality of distinct data, an image delivered by the imaging device being formed by juxtaposing the distinct data, the pixelated detector being placed so as to detect x-ray photons potentially scattered by the object, an absorbing plate pierced with at least one orifice allowing x-ray photons potentially scattered by the object to pass through the orifice, the pixelated detector being placed so as to detect x-ray photons passing through the orifice.

The one or more orifices may each form a diaphragm through which x-ray photons pass, between the object and the pixelated detector. Alternatively, the absorbing plate may be pierced with a plurality of orifices and form a collimator that is tailored to the pixelated detector, and that lets only x-ray photons moving substantially in a predefined direction pass through.

In this particular embodiment, the various x-ray sources are advantageously evenly distributed around the orifice.

Each x-ray source advantageously comprises a cold cathode that emits an electron beam via a field effect.

The imaging device may comprise one of the x-ray sources. The control module may be configured to make a plurality of sources emit simultaneously or to make one or more sources among the control module x-ray sources emit sequentially.

Each x-ray source is advantageously configured to irradiate, at a given time, the entirety of the analysis region.

In this particular embodiment of the invention, the absorbing plate may comprise a plurality of orifices. The imaging device then comprises a module for processing signals delivered by the detector, the processing module being configured to extract the useful information representing the image of the object to be imaged.

BRIEF DESCRIPTION OF THE DRAWINGS

The invention will be better understood and other advantages will become apparent on reading the detailed description of one embodiment given by way of example, the description being illustrated by the attached drawing, in which.

For the sake of clarity, the same elements have been designated by the same references in the various figures.

DETAILED DESCRIPTION

Figure 1:
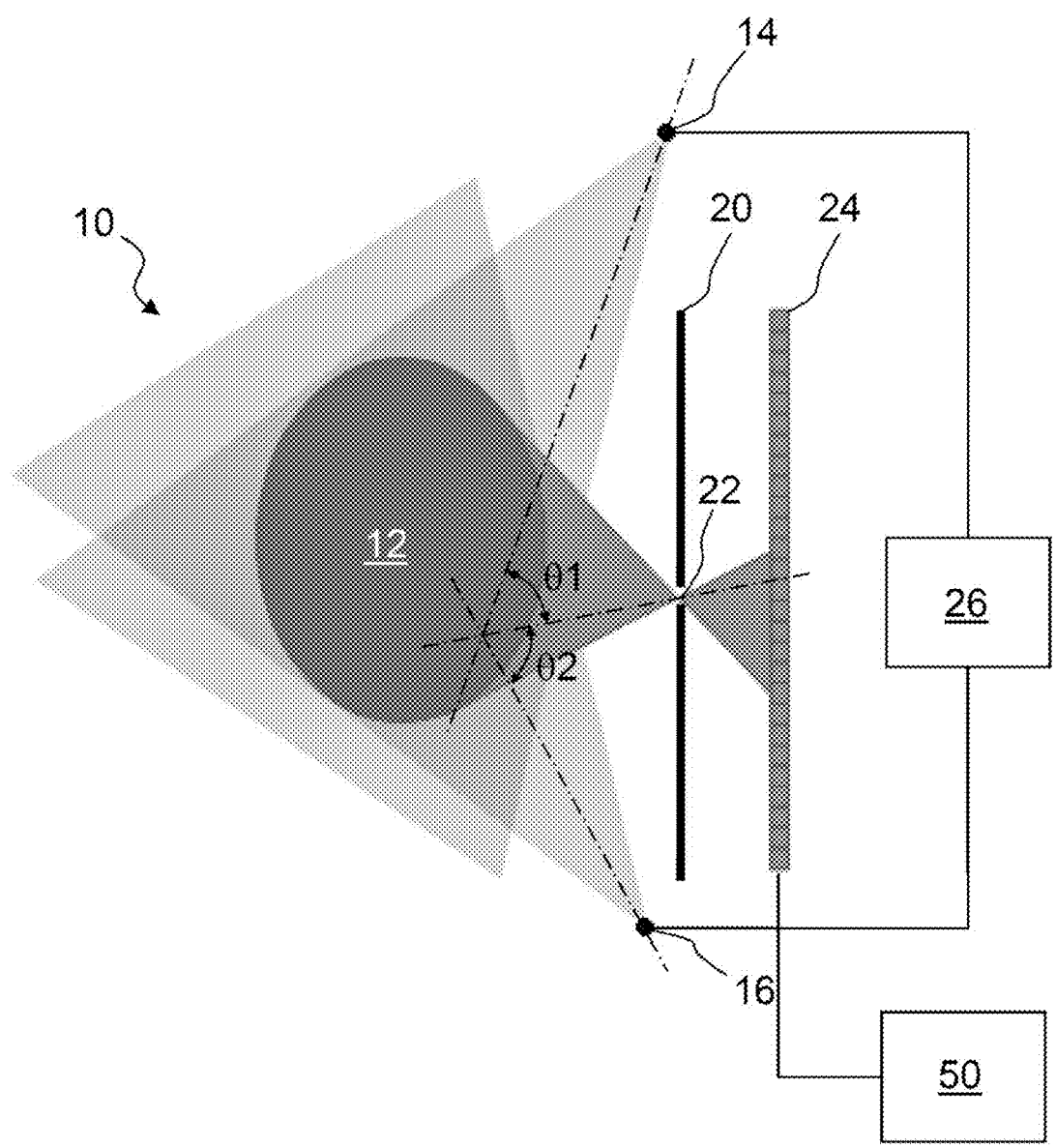
FIG. 1 schematically shows one example of an imaging device according to the invention.

FIG. 1 schematically shows one example of an imaging device 10 according to the invention allowing backscattered x-ray photons to be detected. The imaging device 10 comprises a plurality of x-ray sources all configured to irradiate an analysis region 12 of the device 10. The objects to be imaged are placed in the analysis region 12. The shape of the beam emitted by each source may be conical and cover the entire analysis region. Thus the sources do not need to be scanned to irradiate the analysis region 12 and all the points of the analysis region 12 are irradiated at the same time by all the x-ray sources. Alternatively, the various sources may be scanned to irradiate the analysis region 12. It is also possible to employ sources that are unable to irradiate the entirety of the analysis region 12, with or without scanning. The presence of a plurality of x-ray sources, even if each cannot irradiate the entirety of the analysis region, alone allows the uniformity of the irradiation of the analysis region 12 to be improved. In the illustrated example, two sources 14 and 16 have been shown. It is of course possible to implement the invention in a device comprising more than two x-ray sources.

The sources 14 and 16 have been schematically shown in FIG. 1 by a dot forming the focal point from which the x-rays originate. In practice, in the context of the invention, any type of x-ray source may be employed, whether it possesses a focal point or not. By way of example, mention may be made of tubes employing a thermionic cathode. Among these tubes, tubes having a fixed anode or tubes having a rotating anode may be used. The latter type of tube has the advantage of better dissipation of the heat emitted when the electron beam emitted by the cathode reaches the anode. It is also possible to employ cold-cathode tubes, in which an electron beam is emitted via a field effect. This type of tube is for example described in patent application WO 2019/011980 A1 filed in the name of the applicant. Cold-cathode x-ray sources have the advantage of compactness, allowing them to be employed, for example, in a portable imaging device 10. Cold-cathode x-ray sources are also smaller in size than sources employing a thermionic cathode, this making it easier to increase the number of sources present in the imaging device 10.

The imaging device 10 is based on the pin-hole principle. To this end, the device 10 comprises an absorbing plate 20. More precisely, the plate is made of a material that absorbs x-rays. The absorbing plate 20 is pierced with at least one orifice 22 allowing x-ray photons scattered by the object to be imaged to pass through the orifice 22. In the variant shown in FIG. 1, the one or more orifices may each form a diaphragm through which x-ray photons pass. The diaphragm has a fixed aperture and may be likened to a pin hole. In practice, the material of the absorbing plate 20 allows most of the radiation reaching it to be absorbed. Materials of high atomic number are used. In a portable device, i.e. in a device where it is sought to decrease overall mass, the inclination might be to decrease the mass of integrated components, and in particular the mass of the absorbing plate 20, in particular by decreasing its thickness, this leading to a decrease in the absorption of the plate 20. The material and thickness of the plate 20 are defined to allow the radiation absorbed by the plate and the radiation passing through the orifice 22 to be discriminated between.

The imaging device 10 further comprises an x-ray detector 24 placed so as to detect x-ray photons passing through the orifice 22. The detector 24 is pixelated so as to identify the region of the object to be imaged by which the scattered photons were delivered. By pixelated detector, what is meant is any type of detector able to simultaneously collect various data in at least one direction. The image delivered by the device 10 is formed by juxtaposing the various data. In other words, the number of distinct data collected by the detector defines the spatial resolution of the image delivered by the device 10. The image is formed via spatial juxtaposition of the various data collected by the detector 24. It may be a question of an analog detector, for example such as a photosensitive film, or of a digital detector possessing a plurality of discrete pixels. In practice, digital detectors typically comprise several thousand to several million pixels. There are many families of digital detectors that may be employed in the context of the invention. By way of example, mention may be made of flat-panel detectors employing indirect detection and possessing a scintillator that converts the x-ray photons into photons at a wavelength suitable for the technology of the detectors. Mention may also be made of flat-panel detectors employing direct detection of x-ray photons. The flat panel extends in two dimensions. It is also possible to employ a strip detector extending in a single direction. It is also possible to employ an optical camera associated with a scintillator. Screens employing photostimulated luminescence may also be used as detector in the context of the invention. This type of screen is commonly used in a particular form of digital radiology often referred to by the acronym CR for Computed Radiography. The principle of this form of radiology consists in forming an image on the screen then in scanning the screen with a dedicated device. The screen is then strongly irradiated so as to erase the image, before being used again.

The invention may also be implemented without an absorbing plate and with a collimated detector. More precisely, a collimated detector makes it possible to receive only photons coming from one direction or having a small angular deviation from this one direction. Photons coming from other directions are absorbed by a collimator placed between the detector and the region 12. This allows, for each pixel of the detector, the region of origin in the object to be determined.

Irradiating the region 12 by means of a plurality of distinct x-ray sources makes it possible to improve not only the uniformity of the irradiation of the region 12 but also the uniformity of the distribution of the backscattered photons over the detector 24. With a single source, two types of non-uniformities are observed. First of all, the distance to the source leads to a non-uniformity in the intensity of the irradiation as a result of the conical spread of the incident beam. The closer a point of the object is to the source, the more incident photons it receives and, consequently, the more scattered photons it emits. It is thus possible to define, for each point of the object, an angle between a first direction passing through the point in question and the source and a second direction passing through the point in question and the orifice 22. For a given flux of incident photons, the intensity of the scattered photons depends on the angle between the two directions. In FIG. 1, an angle θ1 and an angle θ2 have been shown for scattering from a point of the object receiving x-ray photons from the two sources 14 and 16, respectively. With a plurality of sources, the two types of non-uniformities due to the distance to the source and due to angle tend to compensate for each other depending on the origin of the incident photons.

In order to best decrease these two types of non-uniformities, the various x-ray sources are evenly distributed around the orifice 22. More precisely, the various sources are distributed around a circle the center of which lies on an axis passing through the orifice 22. In the example shown, the two sources 14 and 16 are radially opposite on the circle defined above. In FIG. 1, the circle is seen from the side.

The imaging device 10 comprises a module 26 for controlling the x-ray sources (14, 16). The control module 26 may be configured so that the various sources can emit simultaneously. Simultaneous emission allows the signal-to-noise ratio of the image of the object obtained by the detector 24 to be improved. Specifically, for a source taken in isolation, the maximum x-ray flux that it may emit is mainly related to its ability to dissipate heat. By multiplying the number of sources, the flux of x-ray photons reaching the object to be imaged is increased accordingly. If, on the contrary, the signal-to-noise ratio of a single source is considered sufficient, by multiplying the number of sources, to reach the same flux of incident x-ray photons, the time for which the various sources emit may be decreased. This allows the integration time of each pixel of the detector 24 to be decreased. In a digital detector, the decrease in integration time allows the impact of the leakage current of each pixel to be decreased and therefore allows the quality of the signals collected and consequently the quality of the image of the object to be improved.

Alternatively or even in addition, it is possible to configure the control module 26 so that the various sources are able to emit sequentially. Sequential emission may be advantageous, in particular to limit the instantaneous power consumption of the device by distributing over time the turn-on of the various x-ray sources. In the device 10, the control module 26 may be configured to allow a user to choose between simultaneous emission and sequential emission. These two types of emission may even be combined by allowing P sources among N to emit simultaneously, N being the total number of sources and P being a natural integer strictly lower than N. The P selected sources rotate sequentially among the N sources.

Figure 2:
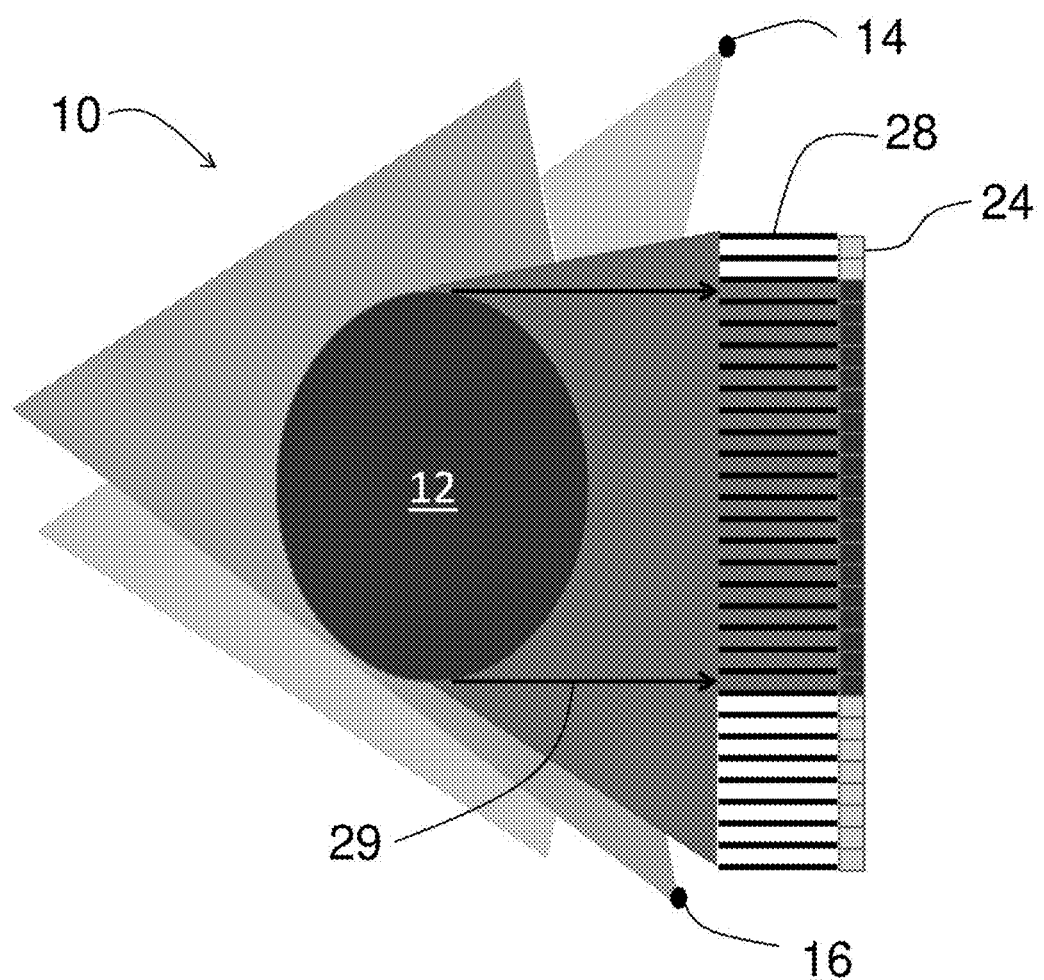
FIG. 2 schematically shows one variant of the device of FIG. 1.

FIG. 2 shows a variant imaging device 10 in which the sources 14 and 16 and the detector 24 are found. Unlike the device 10 of FIG. 1, the absorbing plate forms a collimator 28 tailored to the detector 24. In other words, the collimator 28 is pierced with a plurality of orifices that let pass through only x-ray photons moving substantially in a predefined direction 29. The collimator 28 has the same area as the detector 24. The pitch of the orifices of the collimator 28 is equal to or a multiple of the pitch of the pixels of the detector 24. In the example shown, the direction 29 is perpendicular to the plane of the detector 24.

X-ray photons diverging from the direction 29 are absorbed by the collimator 28. In FIG. 2, pixels of the detector 24 receiving x-ray photons having passed through the collimator 28 have been shaded a darker gray than the other pixels.

In the variant of FIG. 1 the image formed on the detector 24 is inverted, whereas in the variant of FIG. 2 it is not.

Figure 3:
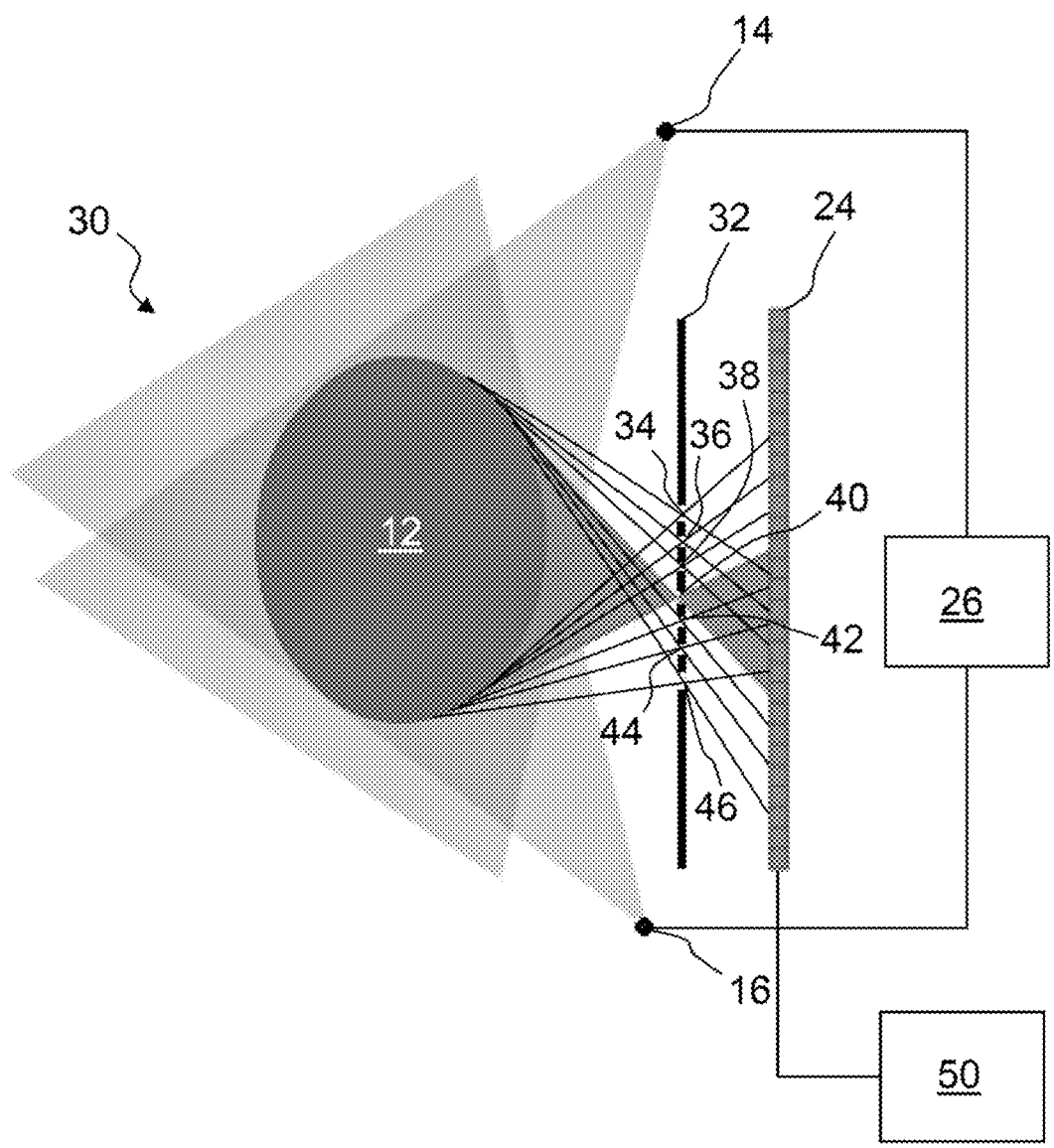
FIG. 3 schematically shows another variant of the device of FIG. 1.

FIG. 3 shows a variant imaging device 30 in which the sources 14 and 16 and the detector 24 are found. Unlike the device 10, the device 30 comprises a plate 32 pierced with a plurality of orifices 34, 36, 38, 40, 42, 44 and 46. In the example shown, the various orifices are distributed along a given axis of the plate 32, the vertical axis in FIG. 3. In practice, in the case of a planar detector 24, the various orifices are distributed over an area of the plate 32, for example one with a circular outline. The orifices may be discrete. More generally, the absorption of the plate 32 varies according to a two-variable function in a spatial coordinate system of the plate. The function may for example be written: f(x, y), x and y being two Cartesian coordinates of the area of the plate 32. The image I(x, y) delivered by the detector depends both on the object, useful data on which it is sought to obtain in an x, y coordinate system: O(x, y), and on the function f(x, y). The imaging device 30 comprises a module 50 for processing signals delivered by the detector 24 and configured to extract the useful information O(x, y) representing the image of the object. The signals delivered by the detector 24 form a convolution of elementary signals resulting from photons having passed through each of the orifices 34 to 46. The processing module 50 advantageously implements a deconvolution-based algorithm to find the image of the object O(x, y). It will be noted that if the images projected onto the detector via the various orifices do not overlap, the deconvolution algorithm approaches a simple superposition of the images, possibly with processing allowing the impact of parallax effects to be decreased.

With respect to the device 10, the device 30 allows the flux of photons reaching the detector 24 and therefore the signal-to-noise ratio of the image to be substantially increased. This improvement is however obtained at the expense of a slight loss of spatial resolution, which may remain acceptable given the increase in image quality due to the improvement in signal-to-noise ratio.

In the various variants, the processing module 50 is configured to deliver the image delivered by the device 10 or 30. More precisely, the processing module 50 collects the data delivered by the detector 24 and juxtaposes them to form an image of the object located in the analysis region 12. When the detector 24 is digital, the processing module 50 receives the data from the various pixels, for example in the form of a charge or a voltage. The processing module 50 may comprise one or more analog-to-digital converters and a multiplexer allowing the image to be delivered in the form of a digital frame. In the case of the detector 30 equipped with the plate 32, the deconvolution processing may be carried out on the digital data downstream of the analog-to-digital converter.

The invention claimed is:

1. An imaging device employing backscattered x-ray photons, comprising:
    a plurality of x-ray sources configured to simultaneously emit x-rays and all configured to irradiate an analysis region in which an object to be imaged is placed,
    a pixelated x-ray detector configured to simultaneously collect a plurality of distinct data, an image delivered by the imaging device being formed by juxtaposing the distinct data, the pixelated detector being placed so as to detect backscattered x-ray photons potentially scattered by the object from the plurality of x-ray sources,
    an absorbing plate pierced with at least one orifice allowing backscattered x-ray photons potentially scattered by the object to pass through the orifice, the pixelated detector being placed so as to detect backscattered x-ray photons passing through the orifice.

2. The imaging device as claimed in claim 1, wherein the one or more orifices each form a diaphragm through which backscattered x-ray photons pass, between the object and the pixelated detector.

3. The imaging device as claimed in claim 1, wherein the absorbing plate is pierced with a plurality of orifices and forms a collimator that is tailored to the pixelated detector, and that lets only backscattered x-ray photons moving substantially in a predefined direction pass through.

4. The imaging device as claimed in claim 1, wherein the various x-ray sources are evenly distributed around the orifice.

5. The imaging device as claimed in claim 4, wherein the various sources are distributed around the orifice in a circle where the center of the circle lies on an axis passing through the orifice.

6. The imaging device as claimed in claim 1, wherein each x-ray source comprises a cold cathode that emits an electron beam via a field effect.

7. The imaging device as claimed in claim 1, comprising a module for controlling the x-ray sources, which module is configured to make one or more sources among the x-ray sources emit sequentially.

8. The imaging device as claimed in claim 1, wherein each x-ray source is configured to irradiate, at a given time, the entirety of the analysis region.

9. The device as claimed in claim 1, wherein the absorbing plate comprises a plurality of orifices, the imaging device comprising a module for processing signals delivered by the detector, the processing module being configured to extract information representing the image of the object to be imaged.

\* \* \* \* \*